United States Patent [19]

Nieh

[11] Patent Number: 4,892,977

[45] Date of Patent: Jan. 9, 1990

[54] PREPARATION OF NONIONIC SURFACTANTS BY OXYALKYLATION WITH A MAGNESIUM CATALYST

[75] Inventor: Edward C. Y. Nieh, Austin, Tex.

[73] Assignee: Texaco Chemical Company, White Plains, N.Y.

[21] Appl. No.: 205,754

[22] Filed: Jun. 13, 1988

[51] Int. Cl.⁴ .............................................. C07C 41/03
[52] U.S. Cl. ................................................... 568/618
[58] Field of Search ............................. 568/618, 620

[56] References Cited

U.S. PATENT DOCUMENTS 4,453,023 6/1984 McCain et al. ...................... 568/624
4,465,877 8/1984 Edwards ............................. 568/618
4,754,075 6/1988 Knopf et al. .

FOREIGN PATENT DOCUMENTS 1185992 4/1985 Canada ................................. 518/618

Primary Examiner—Howard T. Mars
Attorney, Agent, or Firm—Jack H. Park; Kenneth R. Priem

[57] ABSTRACT

Nonionic surfactants containing a narrow molecular weight distribution is obtained by the use of a magnesium-containing catalyst which comprises reacting a reactive hydrogen compound selected from the group consisting of monohydric alcohols having from about 6 to 30 carbon atoms with an alkylene oxide having from 2-4 carbon atoms at a temperature at which the reaction proceeds in the presence of at least a catalytic amount of a particular magnesium catalyst containing phosphorus.

12 Claims, No Drawings

PREPARATION OF NONIONIC SURFACTANTS BY OXYALKYLATION WITH A MAGNESIUM CATALYST

This application is related to application Ser. No. 205,753 filed of even date.

BACKGROUND OF THE INVENTION

The present invention relates to a process for preparation of nonionic surfactants wherein the molecular weight distribution of the nonionic surfactants obtained is in a narrow range.

The instant invention relates to the preparation of improved nonionic surfactant active agents and more particularly, to a process for the oxyalkylation of certain reactive hydrogen compounds to prepare nonionic surfactant active agents wherein the molecular weight distribution is narrow and wherein a novel magnesium-containing catalyst is employed to produce the nonionic surfactants.

Low molecular weight condensation products of an alkylene oxide, particularly ethylene oxide, or mixtures of alkylene oxides such as ethylene and propylene oxide with an alcohol are well known and for a long time have been prepared commercially for use in detergents, cleansing agents, dry cleaning materials, wetting and emulsifying agents and the like. These products are conventionally produced by reacting the reactive hydrogen compound with the alkylene oxide in the presence of a strongly alkaline or an acidic catalyst. Such preparative procedures result in the production of a mixture of relatively low molecular weight (up to about 2000) condensation product species containing a number of alcohol derivatives having different molecular proportions of alkoxylate. Thus, the reaction products generally obtained are, in reality, a mixture of derivatives of the alcohol moiety containing different molecular proportions of alkylene oxide units, i.e., having varying molar ratios of alcohol to alkylene oxide, and a wide range of molecular weights as well as having a certain proportion of unreacted alcohol. Moreover, as is well known, the conventional designation of the number of alkylene oxide units present per molecule of an alcohol alkoxylate is a designation of the average number of alkylene oxide units per molecule and that a substantial proportion of the alcohol alkoxylates present are present as alcohol alkoxylates having a greater and a lesser number of alkylene oxide units present than the actual average value would indicate. Such designations of such products is well understood in the art and will be employed herein consistent with is well understood meaning.

It is generally desirable to restrict, i.e. control the breath of the molecular weight distribution of the mixture to adjacent analogues of the desired product insofar as possible, since, as is well known, the number of moles of alkylene oxide in the reaction product is a major factor in determining what the properties of such products are, but as a matter of course it is quite difficult to control the molecular weight distribution. Acidic catalysts tend to give a narrower molecular distribution than alkaline catalysts, but, unfortunately, also contribute to the formation of undesired by-products. Thus, alkaline catalysts which are typically a strong base such as alkali metal hydroxides and alcoholates are generally used as the more efficient type of oxyalkylation catalyst, but the molecular distribution of the products are more diffuse, containing a greater proportion of lower and higher molecular weight species and smaller amounts of the species with the desired number of moles of alkylene oxide per mole of alcohol. For example, an 8-mole ethylene oxide (EO) adduct per mole of 1-dodecanol will contain not only the 8-mole EO adduct specie but also lower mole adducts and higher mole adducts. Lower mole adducts in the product mixture will range down to the one-mole adduct and higher adducts will extend up to 14 or 15 and beyond. The molecular weight ditribution is a measure of the relative amounts of the various adducts in the product mixture and can be represented in the form of a generally bell-shaped curve where the amount of each adduct species is plotted versus the number of moles of epoxide in the specie or of a description of the relative amount of each individual adduct. When the molecular weight distribution is characterized by a bell-shaped curve, a narrower distribution gives a sharper curve which is, higher at the middle and lower at the ends. A broader distribution curve would be lower at the middle portion of the range and higher at the ends, and such is not desirable.

Heretofore, several methods have been suggested for providing reaction products of an active hydrogen compound, e.g., alcohol, and epoxides which have a narrower range of molecular weights and molecular distribution of the epoxide units, and/or which reduce or eliminate the production of undesirable poly(alkylene glycol) and cyclic and straight chain ether by-products. For example, in U.S. Pat. No. 4,112,231 to Weibull et al it is disclosed that the use of certain neutral inorganic fluoborate and perchlorate salts will catalyze the reaction of epoxides with active hydrogen compounds to give products having a relatively narrower molecular distribution, i.e., a more limited range of molecular species and a larger proportion of desire molecular species; in U.S. Pat. No. 3,682,849 to Smith et al improved ethoxylated derivatives in $C_{11}$–$C_{18}$ alcohols are prepared by removing unreacted alcohol and lower ethoxylates from the ethoxylate mixture prepared by conventional methods by use of vapor phase separation techniques; in U.S. Pat. No. 2,870,220 to Carter, a two-stage process is disclosed for preparing monoalkyl ethers of ethylene glycol and polyethylene glycols of more restricted molecular weight range wherein an alkanol and ethylene oxide is reacted in the presence of an acidic catalyst during the first stage and then in the second-stage after removal of acid catalyst and unreacted alkanol, reacting the mixture with ethylene oxide in the presence of an alkali metal alcoholate of the initial alkanol; and in U.S. Pat. No. 3,972,948 to Laemmle et al there is disclosed a method of preparing mono- and polyglycol ethers substantially free of undesired alkylene glycol by-products which method involves heating a reaction mixture containing an alkylene oxide and an alcohol in the presence of a catalyst containing alkali or alkaline earth cations wherein some or all of the catalyst is an anhydrous high boiling liquid residue prepared by concentrating the liquid residue from the same or different etherification processes after removal of the glycol ether product from the reaction mixture. None of the above-described processes and special catalysts disclosed in the art, however, are completely satisfactory in preparing a product with a desired molecular distribution in that such generally require multi-stage procedures or special acid-resistant equipment, may form undesirable by-products or simply do not provide sufficient control over the molecular weight distribution to be of a satisfactory nature. Thus, it would be highly desirable to develop a process where in the reaction of an alkylene oxide (epoxide) with an alcohol could be more readily carried out to prepare surfactant products that have a relatively narrower molecular weight distribution of analogue species and contain only small amounts, at most, of undesirable poly(alkylene glycol) and ether by-products.

Several patents are concerned with the preparation and advantages of nonionic surfactant products having a narrower molecular weight distribution. For example, U.S. Pat. No. 4,239,917 to Yang discloses the use of a class of basic barium materials as catalysts in the preparation of reaction products of alcohols and ethylene oxide so as to provide a product with a narrow, high mole adduct distribution while providing relatively low levels of undesirable by-products and unreacted free alcohol. The molecular weight distribution factor of the products produced during the oxyalkylation reaction is discussed at length by patentee and the differences in the molecular weight distribution of reaction products prepared with conventional alkali metal catalysts such as sodium hydroxide and those prepared using a barium catalyst of the invention is shown by graphical representations. The patent, to Yang, also shows that other alkaline earth metal materials, such as calcium hydroxide, magnesium oxide, and strontium hydroxide, were ineffective as catalysts for the oxyalkylation reaction. Thus patentee demonstrates that significant differences exist in catalytic effectiveness even between the various alkaline earth metals and not only between the barium catalysts of the invention and alkali metal hydroxides.

Further, U.S. Pat. Nos. 4,210,764 and 4,223,164 to Yang et al are concerned with the problem of the molecular weight distribution of products prepared by oxyalkylation of alcohols using conventional alkaline catalysts and are directed to overcoming an induction period problem frequently observed when employing barium-containing catalysts, such as those disclosed in U.S. Pat. No. 4,239,917. The patentees suggest the use of various phenols for use as a promoter for the barium-containing catalyst to overcome the induction period difficulty, and U.S. Pat. No. 4,223,164, disclose that with such promoters certain basic strontium materials may also be employed as a catalyst for the oxyalkylation reaction.

U.S. Pat. No. 4,453,022 describes the process for preparing nonionic surfactants containing a narrow molecular weight distribution by the use of a catalytic amount of a basic salt of calcium and/or strontium selected from the group consisting of hydroxide, alkoxide and phenoxide and a catalytic amount of an oxyalkylation catalyst promoter.

U.S. Pat. No. 4,721,817 describes alkylene oxide adducts of higher alkanols characterized by relatively narrow range distribution of alkylene oxide adducts by the use of a catalytically effective amount of a catalyst which combines one or more phosphorus-containing acids with one or more aluminum compounds selected from the group consisting of aluminum alcoholates and aluminum phenolates.

European Patent App. No. 0,082,569 shows alkanol soluble basic compounds of magnesium (which could include magnesium alkoxide) activated by alcohol ethoxylate.

It is believed that the instant invention provides an improved method for making narrow range oxyalkylation products using a novel catalyst containing magnesium and phosphorus.

SUMMARY OF THE INVENTION

In accordance with the present invention, there is provided a process and a catalyst for carrying out the process for the preparation of nonionic surfactants having a molecular weight distribution which is narrow. The process comprises reacting a reactive hydrogen compound selected from the group consisting of monohydric primary alcohols having between 6 and 30 carbon atoms, both branched and linear, with an alkylene oxide having 2-4 carbon atoms at a temperature at which the reaction proceeds in the presence of at least a catalytic amount of a catalyst that is produced from the reaction of an alkaline magnesium compound and a phosphorus containing acid or ester. The alkaline magnesium component is the magnesium alkoxide of the alkanol or magnesium phenoxide. The alkaline magnesium component may be generated in situ, for example, by mixing a high molecular weight alkanol with magnesium and low molecular weight alcohol(s) and the subsequent removal of the low molecular weight alcohol(s). The resulting magnesium-containing compound may then be reacted, for example, with phosphoric acid to produce the catalyst of the invention.

DESCRIPTION OF THE PREFERRED EMBODIMENTS

The process of the invention comprises reacting a reactive hydrogen compound selected from the group consisting of monohydric primary alcohols having between 6 and 30 carbon atoms, more preferably between about 10 and 24 carbon atoms and especially preferably liner alkyl primary alcohols comprising from about 6-30 carbon atoms or their mixture with an alkylene oxide having 2-4 carbon atoms in the presence of an oxyalkylation catalyst comprising a catalytically effective amount of a catalyst that is produced from the reaction of an alkaline magnesium compound and a phosphorus containing acid or ester. The alkaline magnesium component is the magnesium alkoxide of the alkanol or magnesium phenoxide. The alkaline magnesium component may be generated in situ, for example, by reacting magnesium with a mixture of high molecular weigth alkohol(s) and low molecular weight alkohol(s) and the subsequent removal of the low molecular weight alcohol. Alternatively, by mixing a high molecular weight alkanol with magnesium alkoxide of low molecular weight alcohol(s) and the subsequent removal of the low molecular weight alcohol(s). The resulting magnesium-containing compound may then be reacted for example, with phosphorous acids or esters to produce the catalyst of the invention.

The reaction may be conducted in a conventional manner, that is, the reactive hydrogen compound and the oxyalkylation catalyst are placed in a reactor, the selected alkylene oxide is added to the reaction mixture until the desired number of moles have been reacted with the reactive hydrogen compound and the product is removed from the reactor and neutralized. The reaction may be conducted in the presence of a solvent, but usually a solvent is not necessary. The process may be batch or continuous.

The temperature at which the reaction proceeds is not especially critical and generally depends upon the desired rate of reaction and sound engineering practices. However, a temperature between about 80° C.

and about 260° C. is usually acceptable with a temperature between about 120 and about 200 being preferred. The pressure likewise of the reaction is not especially critical, however, the use of ethylene oxide and/or propylene oxide as the alkylene oxide usually requires a pressurized reactor. In general the pressure may range between about 20 psig and 200 psig.

The reaction product may be neutralized and catalyst residue removed with any conventional technique known to those skilled in the art.

Alcohols which are suitable for the practice of the invention as the reactive hydrogen compound are monohydric primary alcohols and alkyl phenol having between about 6 and about 30 carbon atoms and especially found useful are linear and branched alkyl primary alcohols of about 8–24 carbon atoms.

Alcohols which are suitable for use in the practice of the invention as the reactive hydrogen compound are primary and secondary aliphatic alcohols which are straight or branched chain and have between about four and about twenty-five carbon atoms. Exemplary of such alcohols are those derived by hydrogenation of natural fats and oils, such as CO and TA alcohols, trademark of and sold by Proctor and Gamble Co., such as CO-1214N alcohol, CO-1618 alcohol, and TA 1618 alcohol, and ADOL alcohols, trade-mark of and sold by Ashland Oil Co., such as ADOL 54 alcohol, ADOL 61 alcohol, ADOL 64 alcohol, ADOL 60 alcohol and ADOL 66 alcohol. Alcohols produced by Ziegler chemistry can also be alkoxylated. Examples of these alchols are ALFOL alcohols, trademarks of and sold by Continental Oil Co., such as ALFOL 1012 alcohol, ALFOL 1214 alcohol, ALFOL 1412 alcohol, ALFOL 1618 alcohol, ALFOL 1620 alcohol; and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohol, trademark of and sold by Shell Oil Co., such as NEODOL 23 alcohol, NEODOL 25 alcohol, NEODOL 1418 alcohol; TERGITOL-L, trademark of Union Carbide Corp., such as TERGITOL-L 125 alcohol; LIAL alcohols, trademark of and sold by Liquichimica Co. such as LIAL 125; and isodecyl and tridecyl alcohols, sold by Exxon Corp., such as isodecyl alcohol and tridecyl alcohol, Guebet alcohols can also be ethoxylated. Representative examples of these alcohols are STANDAMUL alcohols, trademark of and sold by Henkel Chemical Co., such as STANDAMUL GT-12 alcohol, STANDAMUL GT-16 alcohol. STANDMUL GT-20 alcohols, STANDAMUL GT-1620 alcohol. Secondary alcohols can also be used, such as TERGITOL 15 alcohol, trademark of and sold by Union Carbide Corp.

Generally, useable alcohols include 1-decanol; 1-undecanol; 1-dodecanol; 1-tricecanol; 1-tetradecanol; 1-pentadecanol; 1-hexadecanol; 1-heptadecanol; 1-octadecanol; 1-nonadecanol; 1-eicosanol; 1-dicosanol; 2-methyl-1-undecanol 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; tetradecanol; 7-tetradecanol; 2-hexadecanol; 3-hexadecanol; 5-hexadecanol; 6-hexadecanol; 7-hexadecanol; 8-hexadecanol; 2-octadecanol; 3-octadecanol; 3-octadecanol; 4-octadecanol; 5-octadecanol; 6-octadecanol; 7-octadecanol; 8-octadecanol; 9-octadecanol; 9-octadecanol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-; undecanol; 3-hexyl-1-hexyl-1-undecanol; 3-hexyltridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol.

Also employable as the reactive hydrogen compound are the difunctional propylene oxide polymers having a molecular weight of 1000 to 2000. The propylene oxide polymers having a molecular weight of 1000 to 2000 contain from 17 to 86 oxypropylene units in the molecular. These compounds are well known, being generally obtained by polymerization of propylene oxide or by the addition of propylene oxide to lower molecular compounds with 2 to 6 carbon atoms containing at least 2 reactive hydrogen atoms.

Alkylene oxides which may be employed in accordance with the invention include those alkylene oxides having between about 2 and about 4 carbon atoms and include, for example, ethylene oxide, 1,2-propylene oxide, and butylene oxides such as 1,2-butylene oxide, and mixtures thereof. The number of moles of alkylene oxies employed according to the present invention may vary widely depending on the reactive hydrogen compound to be adducted and the particular application for which the surface active agent is to be employed. In general, between about 2 and about 80 or greater moles of alkylene oxide per mole of reactive hydrogen compound may be employed with greater molar ratios being employed if higher molecular weight products are desired. Insofar as propylene oxide and/or butylene oxide are used in combination with ethylene oxide, the molar ratio of ethylene oxide to propylene oxide or butylene oxide may be between about 100:1 and about 3:1, preferably between 50:1 to 5:1.

In the process of this invention, the reaction of an alkylene oxide with a reactive hydrogen compound is carried out in the presence of an oxyalkylation catalyst comprising a product produced from the reaction of an alkaline magnesium compound and a phosphorus-containing acid or ester. More specifically, the alkaline magnesium component is the magnesium alkoxide of the alkanol or magnesium phenoxide. The alkaline magnesium component can be generated in situ by various means, for example, by mixing the high molecular weight alkanol with magnesium alkoxide of low molecular weight alcohols and the subsequent removal of the low molecular weight alcohol or by reacting magnesium halide with sodium alkoxide of the high molecular weight alcohol and the subsequent removal of sodium halide or reacting the high molecular weight alcohol with alkaline magnesium compounds such as diethyl magnesium, dicyclopentadienyl magnesium, magnesium ammoniate, magnesium amide and magnesium thiophenolate.

The phosphorus compounds are selected from orthophosphoric acid, pyrophosphoric acid, alkyl or aryl substituted phosphonic acid or phosphinic acid. The $C_1$ to $C_4$ alkyl ester of the above disclosed acids are also useful.

The active alkoxylation catalyst is generated in situ by adding the phosphorus compound to alkanol containing the magnesium alkoxide. The preferred magnesium to phosphorus ratio is from about 2:1 to about 1:1.

The reaction scheme below shows a general method of making a catalyst suitable for this invention. The structures shown are believed to be accurate but the exact structures have not been characterized by analysis. The method shown is for illustration of the method for preparing a catalyst of the invention.

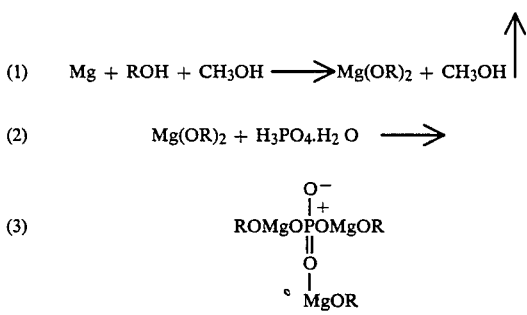

where
R is $C_6$ to $C_{30}$

The above reaction scheme shows the use of methanol and phosphoric acid. It is of course acceptable to use other low molecular weight alcohols such as ethanol and isopropanol, for example and also above disclosed phosphorus acids and esters. The useful high molecular weight alcohols shown as ROH in reaction (1) are the same as those described above as the reactive hydrogen compounds.

The catalyst of the invention produces narrow range alkoxylates that contain less oil soluble oligomers and less water soluble oligomers thus enhancing their usefulness. The peak of molecular weight distribution is especially sharp using the process of this invention. As the data will show, this invention produces products containing less of the unreacted alcohol and 1 to 2 mole adducts of alkylene oxide that affect the per formance of the product distribution.

EXAMPLE 1

Magnesium methoxide was prepared by reacting magnesium turnings (60 grams) with anhydrous methanol (1000 grams) in a 2-liter three-neck flask fitted with stirrer, condenser, thermometer and nitrogen inlet. Magnesium turnings were adeed in 6 gram portions every ten to twelve minutes. Occasionally an ice water bath was used to control reaction temperature in the 35° to 45° C. range. Crystalline magnesium methoxide was obtained after the nearly clear super saturated magnesium methoxide solution in methanol was allowed to stand overnight. The solubility of magnesium methoxide in methanol was estimated to be 1000 ppm by atomic absorption analysis of the mother liquor. Crystalline magnesium methoxide was collected and dried in a vacuum overnight at 50° C. and 20 mm Hg pressure for several hours.

EXAMPLE 2

The preferred magnesium alkoxide catalyst concentrate was prepared by reacting magnesium turnings (61 grams) with a mixture of anhydrous methanol (940 grams) and EPAL 1214 alcohol (1000 grams, a mixture of dodecanol and tetradecanol, average molecular weight 197, available from Ethyl Corp.) in a three-liter three-neck flask fitted with stirrer, condenser, thermometer, and nitrogen inlet. The magnesium turnings were added in small portions every 10 to 12 minute periods. Occasionally, an ice water bath was used to control reaction temperature at 35° to 45° C. When all the magnesium turnings were reacted and a trace quantity of suspended solid by-product had settled, the magnesium alkoxide catalyst concentrate containing 3.0 weight percent soluble magnesium remained as a stable clear solution.

EXAMPLE 3

By a procedure similar to Example 2, a 4.0 weight percent magnesium catalyst concentrate was prepared from magnesium turnings (82 grams), EPAL 1214 alcohol (1000 grams) and methanol (920 grams).

EXAMPLE 4

To a clean, dried one-gallon kettle was charged EPAL 1214 alcohol (1870 grams) and magnesium methoxide catalyst prepared in Example 1 (24 grams). The kettle was heated to 80° at 20 mm Hg pressure in order to strip off methanol. Then, ethylene oxide was added at 165° C. and 80 psi until the desired degree of ethoxylation was reached. The product was neutralized with acetic acid (34 grams). Results were given in Table 1.

EXAMPLE 5

To a clean, dried one-gallon kettle was charged EPAL 1214 alcohol (1750 grams) and magnesium catalyst (11.4 gram-atom Mg, introduced as a catalyst concentrate together with EPAL 1214 alcohol, 121 grams, in a methanol solution). After stripped off methanol, ethylene oxide was added in the same manner as described in Example 4. Results were given in Table 1.

EXAMPLE 6

To a clean and dried one-gallon kettle was charged EPAL 1214 alcohol (1686 grams) and magnesium catalyst (11.4 gram-atom Mg, introduced as a catalyst concentrate together with 184 grams of EPAL 1214 alcohol in a methanol solution). After stripped off methanol, ethylene oxide was added at 150° C. and 50 psi pressure. The product was neutralized with acetic acid (108 grams). Results were given in Table 1.

EXAMPLE 7

To a clean and dried one-gallon kettle was charged EPAL 1214 alcohol (1586 grams) and magnesium catalyst (22.8 gram-atom Mg, introduced as a catalyst concentrate together with 284 grams of EPAL 1214 alcohol in a methanol solution). After stripped off methanol, ethylene oxide was added at 165° C. and 80 psi pressure. The product was neutralized with acetic acid (108 grams). Results were given in Table 1.

EXAMPLE 8

To a clean and dried one-gallon kettle was charged EPAL 1214 alcohol (1764 grams) and magnesium catalyst (6.8 gram-atom Mg, introduced as a catalyst concentrate together with 116 grams of EPAL 1214 alcohol in a methanol solution). After stripped off methanol, at 80° C. and 20 mm Hg pressure, concentrated phosphoric acid 85% in water 10.9 grams) was added. The kettle was again evacuated to 20 mm Hg and heated to 120° C. in order to strip off water. Ethylene oxide was added at 150° C. and 50 psi pressure over a period of 2.75 hours. The product was neutralized with acetic acid (17 grams). Results are given in Table 1 as Example 8A. This Example was repeated and results are given in Table 1 as Example 8B.

EXAMPLE 9

Ethoxylation of EPAL 1214 alcohol was conducted in the same manner as in Example 8 except that magnesium catalyst 5.0 mole % (11.4 gram-atom Mg) was used in place of 3.0 mole % (6.8 gram Mg). Results are given in Table 1.

EXAMPLE 10

Ethoxylation of EPAL 1214 alcohol was conducted in the same manner as in Example 8 except that 98% phosphoric acid (9.5 grams) was used in place of 85% phosphoric acid. Results are given in Table 1.

EXAMPLE 11

Ethoxylation of EPAL 1214 alcohol was conducted in the same manner as in Example 8 except that 97% phosphorous acid (7.8 grams) was used in place of 85% phosphoric acid. Results are given in Table 1.

EXAMPLE 12

Ethoxylation of EPAL 1214 alcohol was conducted in the same manner as in Example 8 except that phosphorus pentoxide (6.7 grams) was used in place of 85% phosphoric acid. Results are given in Table 1.

To illustrate that the magnesium alkoxide activated by phosphoric acid or phosphorus acid in an ethoxylation reaction produced products that have better oligomer distribution than those made with prior art catalyst, the following examples are provided.

EXAMPLES 13 TO 16

Ethoxylation of EPAL 1214 alcohol was conducted using magnesium catalyst concentrate and phosphoric acid to 2.0, 2.5, 3.5 and 4.0 mole ethoxylates.

EXAMPLE 17

The ethoxylation of EPAL 1214 alcohol using magnesium catalyst concentrate and phosphorous acid to a 3.5 mole ethoxylates.

The ethoxylations were conducted in the same manner as disclosed in Example 8 except that 97% phosphorous acid (7.8 grams) was used in place of 85% phosphoric acid. Results are given in Table 2.

EXAMPLE 18

The ethoxylation of EPAL 1214 alcohol using magnesium catalyst concentrate and phenylphosphonic acid.

Ethoxylation of EPAL 1214 alcohol was conducted in the same manner as in Example 8 except that phenylphosphonic acid (22.5 gram) was used in place of 85% phosphoric acid. Results are given in Table 3.

EXAMPLE 19

The ethoxylation of EPAL 1214 alcohol using magnesium catalyst concentrate and phenylphosphinic acid.

Ethoxylation of EPAL 1214 alcohol was conducted in the same manner as in Example 8 except that phenylphosphinic acid (40 grams) was used in place of 85% phosphoric acid. Results are given in Table 3.

EXAMPLE 20

The ethoxylation of EPAL 1214 alcohol using magnesium catalyst concentrate and dimethyl phosphite.

Ethoxylation of EPAL 1214 alcohol was conducted in the same manner as in Example 8 except that dimethyl phosphite (15.6 grams) was used in place of 85% phosphoric acid. Results are given in Table 3.

EXAMPLE 21

The ethoxylation of EPAL 1214 alcohol using magnesium catalyst concentrate and pyrophosphoric acid.

Ethoxylation of EPAL 1214 alcohol was conducted in the same manner as in Example 8, except that pyrophosphoric acid (12.6 grams) was used in place of 85% phosphoric acid. Results are given in Table 3.

Table 4 showing the Poisson distribution is given to illustrate the advantages of my invention. For example, in some cases alkoxylation products prepared using the catalyst of my invention have a range of oligomers comparing favorably with the Poisson distribution. For example, compare Example 8B shown on Tables 1 and 2 with the Poisson distribution as well as those shown in the prior art patents.

TABLE 1

| ETHOXYLATION OF EPAL 1214 ALCOHOL | | | | | | | | | | |
|---|---|---|---|---|---|---|---|---|---|---|
| EXAMPLE NO. | 4 | 5 | 6 | 7 | 8A | 8B | 9 | 10 | 11 | 12 |
| CATALYST, Mole % | | | | | | | | | | |
| Magnesium Alkoxide | 5.00 | 5.00 | 10.00 | 10.00 | 3.00 | 3.00 | 5.00 | 3.00 | 3.00 | 3.00 |
| Phosphoric Acid, 85% | | | | | 1.00 | 1.00 | 1.00 | | | |
| Phosphoric Acid, 98% | | | | | | | | 1.00 | | |
| Phosphoric Acid, 97% | | | | | | | | | 1.00 | |
| Phosphorus Pentoxide | | | | | | | | | | 0.50 |
| REACTION CONDITIONS | | | | | | | | | | |
| Temperature C. | 165 | 165 | 150 | 165 | 150 | 150 | 150 | 150 | 150 | 150 |
| Pressure Psig | 80 | 80 | 50 | 80 | 50 | 50 | 50 | 50 | 50 | 50 |
| Addition Time Hr | 3.80 | 5.00 | 5.00 | 4.20 | 1.92 | 2.12 | 1.97 | 1.55 | 3.75 | 9.50 |
| PRODUCT | | | | | | | | | | |
| # Ave. MW | 379 | 496 | 512 | 495 | 497 | 492 | 516 | 500 | 501 | 478 |
| # Mole EO | 4.14 | 6.80 | 7.16 | 6.80 | 6.80 | 6.70 | 7.25 | 6.90 | 6.90 | 6.38 |
| PEG % | 0.45 | 0.75 | 0.27 | 0.50 | 3.60 | 2.17 | 1.97 | 1.55 | 1.78 | 1.07 |
| Peak+/−2EO Wt % | 74.14 | 66.70 | 64.50 | 66.50 | 75.20 | 77.60 | 71.60 | 74.50 | 74.01 | 67.90 |

TABLE 1-continued

ETHOXYLATION OF EPAL 1214 ALCOHOL

| EXAMPLE NO. | 4 | 5 | 6 | 7 | 8A | 8B | 9 | 10 | 11 | 12 |
|---|---|---|---|---|---|---|---|---|---|---|
| OLIGOMERS | | | | | | | | | | |
| 0EO | 3.19 | 0.57 | 0.06 | 0.77 | 0.68 | 0.53 | 0.74 | 0.70 | 0.15 | 0.07 |
| 1EO | 3.45 | 0.62 | 0.41 | 0.36 | 0.20 | 0.12 | 0.10 | 0.17 | 0.28 | 0.44 |
| 2EO | 8.38 | 1.45 | 1.24 | 1.33 | 0.63 | 0.64 | 0.60 | 0.65 | 0.79 | 1.38 |
| 3EO | 14.55 | 3.24 | 3.12 | 3.69 | 2.21 | 2.36 | 1.90 | 2.00 | 2.44 | 3.48 |
| 4EO | 18.12 | 6.11 | 5.88 | 6.42 | 5.42 | 5.73 | 4.36 | 5.26 | 5.65 | 6.31 |
| 5EO | 17.58 | 8.89 | 9.30 | 10.36 | 11.08 | 11.66 | 8.98 | 10.45 | 10.70 | 10.44 |
| 6EO | 14.29 | 11.54 | 12.46 | 13.89 | 16.39 | 16.87 | 14.20 | 15.72 | 15.60 | 15.74 |
| 7EO | 9.60 | 13.31 | 14.74 | 15.79 | 18.77 | 19.54 | 16.93 | 18.67 | 18.19 | 14.80 |
| 8EO | 5.45 | 12.72 | 14.39 | 14.28 | 16.58 | 17.52 | 16.82 | 16.82 | 16.69 | 12.43 |
| 9EO | 3.04 | 9.22 | 12.65 | 12.14 | 12.35 | 12.30 | 14.05 | 12.83 | 12.82 | 8.82 |
| 10EO | 1.44 | 4.48 | 10.85 | 8.77 | 7.64 | 7.10 | 9.82 | 8.12 | 8.18 | 5.60 |
| 11EO | 0.66 | 3.21 | 6.85 | 5.69 | 4.12 | 3.47 | 5.91 | 4.48 | 4.54 | 3.16 |
| 12EO | 0.21 | 1.51 | 4.43 | 3.20 | 2.05 | 1.41 | 3.16 | 2.17 | 2.16 | 1.57 |
| 13EO | | | 2.47 | 1.89 | 0.99 | 0.63 | 1.58 | 1.00 | 0.95 | 0.75 |
| 14EO | | | 1.28 | 0.92 | 0.51 | 0.36 | 0.45 | 0.49 | 0.42 | 0.29 |
| 15EO | | | 0.57 | 0.36 | 0.22 | 1.41 | 0.26 | 0.25 | 0.22 | 0.14 |
| 16EO | | | 0.17 | 0.10 | 0.11 | 0.63 | | 0.16 | 0.16 | |
| 17EO | | | | 0.92 | | 0.36 | | | | |
| 18EO | | | | 0.36 | | | | | | |
| 19EO | | | | | | | | | | |
| 20EO | | | | | | | | | | |

TABLE 2

ETHOXYLATION OF DETERGENT ALCOHOLS COMPARATIVE EXAMPLES

| | Example | | | | U.S. Pat. No. 4,721,817 Example | | | U.S. Pat. No. 4,453,022 Example | | Example |
|---|---|---|---|---|---|---|---|---|---|---|
| | 13 | 14 | 15 | 16 | 2 | 3 | 4 | 4 | 33 | 8B |
| CATALYST, Mole % | | | | | | | | | | |
| Mg Alkoxide | 3.00 | 3.00 | 3.00 | 3.00 | | | | | | 3.00 |
| Al Isopropoxide | | | | | 1.30 | 0.065 | 0.065 | | | |
| Ca Alkoxide | | | | | | | | 4.00 | | |
| Sr Alkoxide | | | | | | | | | 2.09 | |
| Phosphoric Acid, 85% | 1.00 | 1.00 | 1.00 | | 0.65 | 0.033 | 0.330 | 1.11 | 0.78 | 1.00 |
| Phosphorous Acid, 97% | | | | 1.00 | | | | | | |
| REACTION CONDITIONS | | | | | | | | | | |
| Temperature C. | 150 | 165 | 150 | 150 | 140 | 140 | 140 | 140 | 140 | 150 |
| Pressure Psig | 50 | 50 | 50 | 50 | 30 | 30 | 30.00 | 60 | 60 | 50 |
| Addition Time Hr | 1.10 | 1.10 | 1.10 | 1.33 | 2.00 | 1.00 | 1.00 | 1.66 | 1.33 | 2.12 |
| PRODUCT | | | | | | | | | | |
| # Mole EO | 2.00 | 2.50 | 3.50 | 3.50 | 3.40 | 2.10 | 2.10 | 7.36 | 6.42 | 6.70 |
| PEG % | 0.45 | 0.75 | 1.54 | 1.24 | 0.60 | 0.90 | 0.40 | ? | ? | 2.17 |
| Peak+/−2EO Wt % | 90.13 | 89.83 | 83.56 | 82.90 | 81.00 | 84.80 | 86.80 | 73.30 | 70.80 | 77.60 |
| OLIGOMERS | | | | | | | | | | |
| 0EO | 5.32 | 4.78 | 1.59 | 2.30 | 2.90 | 11.40 | 9.70 | 3.20 | 2.20 | 0.53 |
| 1EO | 14.94 | 8.40 | 3.76 | 2.52 | 4.70 | 16.50 | 18.50 | 0.50 | 1.60 | 0.12 |
| 2EO | 24.58 | 19.00 | 10.89 | 7.89 | 11.00 | 23.80 | 25.60 | 1.00 | 2.80 | 0.64 |
| 3EO | 26.22 | 24.67 | 19.24 | 16.57 | 17.50 | 23.40 | 22.80 | 2.30 | 5.70 | 2.36 |
| 4EO | 16.44 | 20.92 | 21.38 | 21.92 | 21.60 | 14.70 | 13.70 | 5.40 | 10.00 | 11.66 |
| 5EO | 7.69 | 13.79 | 19.54 | 20.65 | 18.40 | 6.40 | 6.20 | 10.30 | 14.70 | 16.87 |
| 6EO | 3.24 | 5.63 | 12.40 | 14.95 | 12.50 | 2.20 | 2.40 | 15.80 | 17.20 | 19.54 |
| 7EO | 1.14 | 1.91 | 6.53 | 8.00 | 6.50 | 0.90 | 0.70 | 18.10 | 16.20 | 17.52 |
| 8EO | 0.43 | 0.87 | 2.57 | 3.40 | 2.00 | 0.40 | 0.20 | 16.50 | 12.70 | 12.30 |
| 9EO | | | 1.26 | 1.35 | 1.40 | | | 12.60 | 8.50 | 7.10 |
| 10EO | | | 0.52 | 0.45 | 0.70 | | | 8.20 | 4.80 | 3.47 |
| 11EO | | | | | 0.50 | | | 4.30 | 2.40 | 1.41 |
| 12EO | | | | | 0.20 | | | 1.60 | 1.00 | 0.63 |
| 13EO | | | | | | | | 0.30 | 0.30 | 0.36 |
| 14EO | | | | | | | | | | |
| 15EO | | | | | | | | | | |
| 16EO | | | | | | | | | | |
| 17EO | | | | | | | | | | |
| 18EO | | | | | | | | | | |
| 19EO | | | | | | | | | | |
| 20EO | | | | | | | | | | |

TABLE 3

ETHOXYLATION OF EPAL 1214 ALCOHOL

| EXAMPLE NO. | 18 | 19 | 20 | 21 |
|---|---|---|---|---|
| CATALYST, Mole % | | | | |
| Magnesium Alkoxide | 3.00 | 3.00 | 3.00 | 3.00 |
| Phenylphosphonic Acid | 1.50 | | | |
| Phenylphosphinic Acid | | 1.50 | | |

TABLE 3-continued
ETHOXYLATION OF EPAL 1214 ALCOHOL

| EXAMPLE NO. | 18 | 19 | 20 | 21 |
|---|---|---|---|---|
| Dimethyl Phosphite |  |  | 1.50 |  |
| Pyrophosphoric Acid |  |  |  | 0.75 |
| REACTION CONDITIONS |  |  |  |  |
| Temperature C. | 150 | 150 | 150 | 150 |
| Pressure Psig | 50 | 50 | 50 | 50 |
| Addition Time Hr | 5.58 | 6.08 | 6.50 | 2.40 |
| PRODUCT |  |  |  |  |
| # Ave. MW | 502.00 | 485.00 | 510.00 | 497.00 |
| # Mole EO | 6.93 | 6.54 | 7.11 | 6.82 |
| PEG % | 2.61 | 8.67 | 2.45 | 1.98 |
| Peak+/−2EO Wt % | 69.10 | 65.10 | 65.40 | 74.11 |
| OLIGOMERS |  |  |  |  |
| 0EO | 0.12 | 0.33 | 0.13 | 0.35 |
| 1EO | 0.32 | 0.64 | 0.36 | 0.32 |
| 2EO | 1.07 | 1.91 | 1.17 | 0.80 |
| 3EO | 3.10 | 4.83 | 3.06 | 2.57 |
| 4EO | 6.47 | 8.27 | 5.94 | 5.97 |
| 5EO | 10.36 | 11.66 | 9.35 | 11.05 |
| 6EO | 14.38 | 14.50 | 13.03 | 16.15 |
| 7EO | 16.22 | 14.82 | 15.02 | 18.26 |
| 8EO | 15.45 | 13.21 | 14.78 | 16.47 |
| 9EO | 12.73 | 10.94 | 13.20 | 12.17 |
| 10EO | 8.76 | 7.37 | 9.57 | 7.46 |
| 11EO | 5.43 | 4.72 | 6.44 | 4.16 |
| 12EO | 2.95 | 2.69 | 3.82 | 1.96 |
| 13EO | 1.44 | 1.51 | 2.12 | 1.02 |
| 14EO | 0.68 | 0.94 | 1.08 | 0.76 |
| 15EO | 0.32 | 0.63 | 0.52 | 0.50 |
| 16EO | 0.19 | 0.53 | 0.28 |  |
| 17EO |  | 0.47 | 0.11 |  |
| 18EO |  |  |  |  |
| 19EO |  |  |  |  |
| 20EO |  |  |  |  |

TABLE 4
POISSON DISTRIBUTION

| PRODUCT |  |  |  |  |  |
|---|---|---|---|---|---|
| # Mole EO | 2.00 | 3.50 | 6.00 | 6.50 | 7.00 |
| Peak+/−2EO Wt % | 92.00 | 81.13 | 68.80 | 66.90 | 65.10 |
| OLIGOMERS |  |  |  |  |  |
| 0EO | 9.40 | 1.70 | 0.10 | 0.10 |  |
| 1EO | 22.90 | 7.27 | 0.80 | 0.50 | 0.30 |
| 2EO | 27.10 | 15.03 | 2.80 | 1.90 | 1.30 |
| 3EO | 20.80 | 20.23 | 6.40 | 4.70 | 3.40 |
| 4EO | 11.80 | 20.06 | 10.80 | 8.60 | 6.70 |
| 5EO | 5.30 | 15.69 | 14.50 | 12.60 | 10.60 |
| 6EO | 1.90 | 10.12 | 16.10 | 15.00 | 13.60 |
| 7EO | 0.60 | 5.54 | 15.10 | 15.30 | 14.90 |
| 8EO | 0.20 | 2.63 | 12.30 | 13.50 | 14.20 |
| 9EO |  | 1.11 | 8.90 | 10.50 | 11.90 |
| 10EO |  | 0.42 | 5.70 | 7.40 | 8.90 |
| 11EO |  | 0.14 | 3.30 | 4.60 | 6.10 |
| 12EO |  | 0.04 | 1.80 | 2.70 | 3.80 |
| 13EO |  | 0.01 | 0.90 | 1.40 | 2.20 |
| 14EO |  |  | 0.40 | 0.70 | 1.10 |
| 15EO |  |  | 0.20 | 0.30 | 0.60 |
| 16EO |  |  | 0.10 | 0.10 | 0.30 |
| 17EO |  |  |  | 0.10 | 0.10 |
| 18EO |  |  |  |  |  |

We claim:

1. A method for the alkoxylation of a reactive hydrogen compound selected from the group comprising monohydric alcohols having between about 6 and about 30 carbon atoms, both branched and linear, with an alkylene oxide having 2 to 4 carbon atoms comprising reacting said monohydric alcohol with said alkylene oxide at a temperature at which the reaction proceeds in the presence of at least a catalytic amount of a catalyst that is produced by (a) mixing a high molecular weight alcohol with magnesium and a low molecular weight alcohol and subsequently removing the low molecular weight alcohol then (b) reacting the resulting magnesium-containing compound with phosphorus acids or esters.

2. A method as in claim 1 wherein the low molecular weight alcohol in Step (a) is methanol and the high molecular weight alcohol in Step (a) has from 6 to 30 carbon atoms.

3. A method as in claim 1 wherein the phosphorus acids or esters are selected from the group consisting of ortho-phosphoric acid, pyro-phosphoric acid, alkyl- or aryl-substituted phosphonic acid or phosphinic acid and their $C_1$-$C_4$ alkyl esters.

4. A method as in claim 1 wherein the low molecular weight alcohol in Step (a) is methanol and the high molecular weight alcohol in Step (a) contains 6 to 30 carbon atoms and the phosphorus acids or esters are selected from the group consisting of ortho-phosphoric acid, pyro-phosphoric acid, alkyl- or aryl-substituted phosphonic acid or phosphinic acid and their $C_1$-$C_4$ alkyl esters.

5. A method as in claim 4 wherein phosphoric acid is used.

6. A method as in claim 4 wherein phosphorus acid is used.

7. A method for the alkoxylation of a reactive hydrogen compound selected from the group comprising monohydric alcohols having between about 6 and about 30 carbon atoms, both branches and linear, with an alkylene oxide having 2 to 4 carbon atoms comprising reacting said monohydric alcohols with said alkylene oxide at temperature at which the reaction proceeds in the presence of at least a catalytic amount of a catalyst that is produced by (a) mixing a high molecular weight alcohol with magnesium alkoxide of low molecular weight alcohol and subsequently removing the low molecular weight alcohol then (b) reacting the resulting magnesium-containing compound with phosphorus acids or esters.

8. A method as in claim 7 wherein the low molecular weight alcohol in Step (a) is methanol and the high molecular weight alcohol in Step (a) has from 6 to 30 carbon atoms.

9. A method as in claim 7 wherein the phosphorus acids or esters are selected from the group consisting of ortho-phosphoric acid, pyro-phosphoric acid, alkyl- or aryl-substituted phosphonic acid or phosphinic acid and their $C_1$-$C_4$ alkyl esters.

10. A method as in claim 7 wherein the low molecular weight alcohol in Step (a) is methanol and the high molecular weight alcohol in Step (a) contains 6 to 30 carbon atoms and the phosphorus acids or esters are selected from the group consisting of ortho-phosphoric acid, pyro-phosphoric acid, alkyl- or aryl-substituted phosphonic acid or phosphinic acid and their $C_1$-$C_4$ alkyl esters.

11. A method as in claim 10 wherein phosphoric acid is used.

12. A method as in claim 10 wherein phosphorus acid is used.